| United States Patent [19] | [11] Patent Number: 4,632,780 |
|---|---|
| Seidah et al. | [45] Date of Patent: Dec. 30, 1986 |

[54] N-TERMINAL FRAGMENT OF HUMAN PRO-OPIOMELANOCORTIN AND PROCESS THEREFOR

[76] Inventors: Nabil G. Seidah, 274 Corot St., Ile des Soeurs, Verdun, Quebec, Canada, H3E 1K7; Michel Chretien, 176 Berkley St., St. Lambert, Quebec, Canada

[21] Appl. No.: 281,928

[22] Filed: Jul. 10, 1981

[51] Int. Cl.$^4$ .......................................... C07C 103/52
[52] U.S. Cl. ..................................................... 530/306
[58] Field of Search ................................. 260/112.5 R

[56] References Cited
PUBLICATIONS

James L. Roberts—Biochemistry, vol. 74, pp. 4826–4830, (1977).
Richard E. Mains—Medical Sciences, vol. 74, pp. 3014–3018, (1977).
Shigetada Nakanishi—Febs Letters, vol. 84, pp. 105–109, (1977).
P. Crine—Biochemistry, vol. 75, pp. 4719–4723, (1978).
James L. Roberts—Biochemistry, 112199/78R, pp. 3609–3618, (1978).
Michael B. Hinman—Biochemistry, 133064/80R, pp. 5395–5402, (1980).
M. Chretien—Canadian Journal of Biochemistry, vol. 57, pp. 1111–1121, (1979).
Richard E. Mains—Journal of Biological Chemistry, vol. 254, pp. 7885–7894, (1979).
N. G. Seidah—Biochemistry, vol. 75, pp. 3153–3157, (1978).
P. Crine—Biochemistry, vol. 76, pp. 5085–5089, (1979).
F. Gossard—Biochemical and Biophysical Research Communications, vol. 92, pp. 1042–1051, (1980).
N. G. Siedah—Annals of the New York Academy of Sciences, vol. 343, pp. 443–446, (1980).
Edward Herbert—Annals New York Academy of Sciences, vol. 343, pp. 78–93, (1980).
Christina Gianoulakis—Journal of Biological Chemistry, vol. 254, pp. 11903–11906, (1979).
A. P. Scott—Nature New Biology, vol. 224, pp. 65–67, (1973).
A. P. Scott—J. Endocr, vol. 70, pp. 197–205, (1976).
Philippe Crine—Eur. J. Biochem, vol. 110, pp. 387–396, (1980).
Shigetada Nakanishi—Nature, vol. 278, pp. 423–427, (1979).
Annie C. Y. Chang—Proc. Natl. Acad. Sci., vol. 77, pp. 4890–4894, (1980).
Shigetada Nakanishi—Nature, vol. 287, pp. 751–755, (1980).
Jacques Drouin—Nature, vol. 228, pp. 610–613, (1980).
Rolf Hakanson—Nature, vol. 263, pp. 189–192, (1980).
Lariviere—Febs. Letters, vol. 122, pp. 279–282, (1980).
Fernando E. Estivariz—Biochem J., vol. 191, pp. 125–132, (1980).
N. G. Seidah—Biochemical and Biophysical Research Communications, vol. 95, pp. 1417–1424, (1980).
S. Benjannet—Nature, vol. 285, pp. 415–416, (1980).
Biochemistry, vol. 11, p. 1726, (1972).
Henry T. Keutmann—Journal of Biological Chemistry, vol. 254, pp. 9204–9208, (1979).
Jean Houmard—Proc. Nat. Acad. Sci., vol. 69, pp. 3506–3509, (1972).
M. Chretien—Biochemical and Biophysical Research Communications, vol. 72, pp. 472–478, (1976).

(List continued on next page.)

*Primary Examiner*—Delbert P. Phillips
*Assistant Examiner*—F. T. Moezie
*Attorney, Agent, or Firm*—Cushman, Darby & Cushman

[57] ABSTRACT

There are disclosed the N-terminal fragment of human pro-opiomelanocortin, a glycopeptide composed of 76 amino acid residues, and a process for preparing same from human pituitary glands. The glycopeptide is useful in potentiating the effects of ACTH on steroidogenesis, in stimulating the production of aldosterone, as a diagnostic tool, as well as a reagent for determining its presence in biological fluids and tissues by immunochemical means.

2 Claims, 10 Drawing Figures

PUBLICATIONS

N. G. Seidah—Journal of Chromatography, vol. 193, pp. 291-292, (1980).

N. G. Seidah—Analytical Biochemistry, vol. 109, pp. 185-191, (1980).

Arthur M. Crestfield—Journal of Biological Chemistry, vol. 238, pp. 622-627, (1963).

Martha Fauconnet—Analytical Biochemistry, vol. 91, pp. 403-409, (1978).

Ralph Somack—Analytical Biochemistry, vol. 104, pp. 464-468, (1980).

N. G. Seidah—Biochemical and Biophysical Research Communications, vol. 100, pp. 901-907, (1981).

Esmond E. Snell—Annual Review of Biochemistry, vol. 45, pp. 217-237, (1976).

Dorothy D. Pless—Proc. Natl. Acad. Sci., vol. 74, pp. 134-138, (1977).

Ellen Li—Journal of Biological Chemistry, vol. 253, pp. 7762-7770, (1978).

Martin Lis—Journal of Clinical Endrocrinology and Metabolism, vol. 52, pp. 1053-1056, (1981).

N-TERMINAL FRAGMENT OF HUMAN PRO-OPIOMELANOCORTIN AND PROCESS THEREFOR

BACKGROUND OF THE INVENTION (a) Field of Invention

The present invention relates to a glycopeptide isolated from human pituitary glands, viz., the N-terminal fragment of human pro-opiomelanocortin (POMC), and to a process for its preparation and purification.

(b) Prior Art

Although adrenocorticotropin (ACTH), beta-lipotropin (beta-endorphin (beta-END), and alpha- and beta-melanocyte-stimulating-hormone (alpha- and beta-MSH) are peptides with markedly different biological activities, yet they have been shown to be synthesized from a common precursor protein in mouse pituitary tumor cells, see e.g. Roberts et al., (1977) Proc. Natl. Acad. Sci. USA 74, 4826–4830, Mains et al., (1977) ibid. 74, 3014–3018, and Nakanishi et al. (1977) FEBS Letters 84, 105–109, and in the anterior and intermediate lobes of the mammalian pituitary, see e.g. Crine et al. (1978) Proc. Natl. Acad. Sci. USA 75, 4719–4723, Roberts et al. (1978) Biochemistry 17, 3609–3618, Hinnman et al. (1980) Biochemistry 19, 5395–5402, and Nakanishi et al. (1977) cited above. In spite of the fact that the two lobes seem to start with similar forms of the precursor, named pro-opiomelanocortin (POMC) see Chrétien et al. (1979), Can. J. Biochem. 57, 1111–1121 who give an exhaustive review of the state of the art, they process these forms into different end products, see Mains et al. (1979) J. Biol. Chem, 254, 7885–7894, Seidah et al. (1978) Proc. Natl. Acad. Sci. USA 75, 3153–3157, Crine et al. (1979) Proc. Natl. Acad. Sci. USA 76, 5085–5089, and Roberts et al. (1978), Hinnman et al. (1980) and Chrétien et al. (1979) cited above. Following excision of a 26 residues signal peptide, pulse-chase studies showed the initial maturation of pro-opiomelanocortin into beta-LPH and a large glycopeptide containing ACTH at its carboxy-terminus, see e.g. Gossard et al. (1980) Biochem. Biophys. Res. Commun. 92, 1042–1051, Seidah et al. (1980) Ann. N.Y. Acad. Sci. 343, 443–446, Herbert et al. (1980) Ann. N.Y. Acad. Sci. 343, 79–93. In the anterior lobe beta-LPH, ACTH and an N-terminal glycopeptide of hitherto unspecified C-terminal length are the end products of processing, see Gianoulakis et al. (1979) J. Biol. Chem. 254, 11903–11906, and Roberts et al. (1978) and Mains et al. (1979), both cited above. In the intermediate lobe, beta-LPH is processed further into gamma-LPH and beta-endorphin, see Crine et al. (1978) Roberts et al. (1978), Chrétien et al. (1979), Mains et al. (1979), Seidah et al. (1978), Crine, et al. (1979), and Gianoulakis et al. (1979) all cited above, and ACTH is converted into alpha-MSH and possibly corticotropin-like-intermediate-lobe-peptide (CLIP), see Scott et al. (1973) Nature (London) New Biol. 244, 65–67, Scott et al. (1976) J. Endocrinol. 70, 197–205, and Mains et al. (1979), Crine, et al. (1979) and Gianoulakis et al. (1979), cited above. From pulse-chase experiments the fate of the N-terminal glycopeptide in this lobe seems to be similar to that of the anterior lobe, see Crine et al. (1980) Eur. J. Biochem. 110, 387–396, and Mains et al. (1979), Seidah et al. (1978) and Gianoulakis et al. (1979) cited above.

The advent of recombinant DNA technology has greatly facilitated studies of the nucleic acid sequence of genes coding for protein precursors. Using such techniques the mRNA sequence of bovine pars intermedia pre-pro-opiomelanocortin was first determined by Nakanishi et al. (1979) Nature 278, 423–427. This was followed by reports on the genomic DNA structures of human, bovine, and rat homologous sequences, see Chang et al. (1980) Proc. Natl. Acad. Sci. USA 77, 4890–4894, Nakanishi et al. (1980), Nature 287, 752–755, and Drouin (1980) Nature 288, 610–613, respectively. From these studies it became apparent that an MSH sequence exists in the N-terminal segment of pro-opiomelanocortin which bears sequence homology to both alpha- and beta-MSH. It was therefore called gamma-MSH by Nakanishi et al. (1979) cited above. Based on the results of pulse-chase experiments (see Crine et al. (1979), Gossard et al. (1980), Seidah et al. (1980) Herbert et al. (1980) Crine et al. (1980), and Gianoulakis et al. (1979), all cited above) the purification and the elucidation of the structures of the N-terminal fragment of human and of porcine pro-opiomelanocortin was attempted. While Hakanson et al. (1979), Nature 283, 789–792, reported on the primary sequence of the first 35 amino acid residues of the porcine homologue, Larivière et al. (1980) FEBS Letters 122, 279–282, obtained a preliminary structure for the first 92 residues based upon tryptic peptide mapping and amino acid analysis. Concerning the human analog, Estevariz et al. (1980) Biochem. J., 191, 125–132, predicted the length of the peptide chain as about 82 amino acid residues based upon amino acid analysis, while Seidah et al. (1980) Biochem. Biophys, Res. Comm. 95, 1417–1424, established the sequence of the first 42 amino acids and showed by tryptic peptide mapping that the gamma-MSH region of the molecule was identical between species, see also Benjannet et al. (1980) Nature 285, 415–416. However, the exact length of the C-terminal sequence has hitherto still remained undetermined.

It has now been found that the N-terminal fragment of human pro-opiomelanocortin may indeed be prepared from fresh or frozen human pituitaries by the process of this invention and is thereby obtained in a substantially pure state which permits its characterization by chemical structure as an unambiguously established sequence of the 76 amino acids contained within its molecule. Furthermore, the nature of said N-terminal fragment as that of a glycopeptide, and the exact location of the glycosylation sites, as well as the presence and exact location of disulfide bridges are also established.

SUMMARY OF THE INVENTION

The three-letter notations used throughout this application for the amino acids or the residues thereof are generally based upon the recommendations of the IUPAC—IUB Commission on Biological Nomenclature, see Biochemistry 11, 1726 (1972), and are supplemented by the single-letter symbols shown in parentheses as follows:

alanine—Ala (A); cysteine—Cys (C); aspartic acid—Asp (D); asparagine—Asn (N); glutamic acid—Glu (E); glutamine—Gln (Q); phenylalanine—Phe (F); glycine—(Gly (G); histidine—His (H); isoleucine—Ile (I); lysine—Lys (K); leucine—Leu (L); methionine—Met (M); proline—Pro (P); arginine—Arg (R); serine—Ser (S); threonine—Thr (T); valine—Val (V); tryptophan—Trp (W); tyrosine—Tyr (Y). In addition, the abbreviation Asx is used to denote asparagine (Asn) and/or aspartic acid (Asp), the abbreviation Glx is used to denote glutamine (Gln) and/or glutamic acid (Glu), and the symbol X denotes an unidentified amino acid residue. All amino acids have the natural or L-configuration.

Other abbreviations used are as follows: ACTH; adrenocortocotropin; beta-LPH, beta-lipotropin; beta-END, beta-endorphin; alpha-MSH, alpha-melanotropin; beta-MSH, beta-melanotropin; POMC, pro-opiomelanocortin; gamma-LPH, gamma-lipotropin; CLIP, corticotropin-like-intermediate-lobe-peptide; gamma-MSH, gamma-melanotropin; MSH, melanotropin-stimulating hormone; HPLC, high performance liquid chromatography; PTH, phenylthiohydantoin; V8, staphylococcal protease V8; T, trypsin; CNBr, cyanogen bromide; TEAF, triethylammonium formate; TEAP, triethylammonium phosphate; RIA, radioimmunoassay; CPase-Y, carboxypeptidase Y; SDS, sodium dodecyl sulfate; GlcN, glucosamine; GalN, galactosamine; pI, isoelectric point, HNT, native human N-terminal glycopeptide; AUFS, absorption units full scale.

The N-terminal fragment of human pro-opiomelanocortin, viz, the glycopeptide of this invention is characterized by being composed of 76 amino acids and represents the part of the N-terminal segment preceding the ACTH/LPH sequence of pro-opiomelanocortin. Microsequencing shows the presence of cysteine at positions 2, 8, 20 and 24 identical to those reported for the bovine, rat and mouse homologues. The presence of about 30% of the molecules missing the first N-terminal amino acid is observed giving rise to a partial sequence with cysteine at positions 1, 7, 19, and 23; a similar phenomenon has been reported by Keutmann et al. in J. Biol. Chem. (1979) 254, 9204–9208, and by Gossard et al. (1980) and by Herbert et al. (1980) both cited above for the rat and the mouse homologues. Two glycosylation sites have been identified on the amino acid chain of the above N-terminal fragment, one of them is located at the asparagine residue in position 65 and represents an N-glycosidic linkage; the other site is on the threonine residue in position 45 and represents an O-glycosidic linkage. The complete amino acid sequence of the above glycopeptide is established by a combination of direct sequencing, of cleaving with cyanogen bromide and sequencing the fragments obtained, of cleaving one of the above fragments with staphylococcal protease V8 to obtain three fractions and determining their respective amino acid compositions, and of confirming the nature of the C-terminal amino acid residue by digestion of the native glycopeptide with carboxypeptidase Y. The location of two disulfide bridges is also established.

The process by which the N-terminal fragment of human pro-opiomelanocortin is prepared from human pituitaries comprises, in sequence, the following steps:

(1) HCl/acetone extraction, (2) NaCl precipitation, (3) dialysis or ultrafiltration, (4) chromatography on carboxymethyl cellulose (CMC), (5) high performance liquid chromatography (HPLC) of the material not retained on CMC as obtained from step (4), and (6) testing of the product obtained in step (5) for homogeneity by repeating HPLC under the same conditions as in step (5), or by SDS polyacrylamide electrophoresis, to obtain the substantially pure native N-terminal fragment, viz., the glycopeptide of this invention.

The procedures used for the characterization of the native, substantially pure N-terminal fragment obtained as above in step (5) and for the elucidation of its structure comprise, not necessarily in sequence, the following steps: amino acid analysis of the reduced and carboxymethylated glycopeptide; determination of the sequence of amino acids in said reduced and carboxymethylated glycopeptide; cyanogen bromide cleavage of the native glycopeptide to obtain three fragments designated as CNBr-I, CNBr-II, and CNBr-III, respectively; amino acid analysis of the latter three fragments, and determination of the amino acid sequences in CNBr-II and CNBr-III; labelling of the native glycopeptide with $^{14}C$-iodoacetamide in the presence of a reducing agent, and determining the amino acid sequence of the $^{14}C$-labelled glycopeptide, thus localizing the cysteine residues at positions 2, 8, 20, and 24; incubating of the fragment CNBr-I obtained as described above with an endopeptidase specifically cleaving peptide bonds involving glutamic acid residues, e.g. staphylococcal protease V8 described by Houmard et al. (1972) Proc. Natl. Acod, Sci. USA 69, 3506–3509, to obtain three fraction designated as CNBr-I-V8-I (residues 1–14), CNBr-I-V8-II (residues 15–19) and CNBr-I-V8-III (residues 20–34), respectively, purifying said last-named fractions by HPLC and determining their respective amino acid compositions, to conclude from the results of the above enzymatic cleavage that disulfide bridges are located between cysteine residues at positions 2 and 8, and at positions 20 and 24; concluding from the fact that the sequence determination of the fragment CNBr-III shows in cycle 12 an unidentifiable product, i.e. at the position 65 where asparagine is expected, and from the fact that a glycosylated phenylthiohydantoin derived from asparagine is not soluble in butyl chloride, i.e. in the solvent used in the sequenator for extracting phenylthiohydantoins, that the asparagine residue in position 65 is glycosylated; and further concluding from the ratio of glucosamine to galactosamine of about 3:1 found in the fragment CNBr-III, and by analogy with other glycosylated peptides containing the sequence Asn-X-Ser that asparagine in position 65 in N-glycosylated; concluding from the fact that the fragment CNBr-II contains glucosamine and galactosamine in a ratio of about 1:2, does not contain the triad Asn-X-Ser/Thr characteristic for N-glycosidic linkages, and contains only threonine in position 45 and no serine or other hydroxylated amino acid residues, that threonine in position 45 is O-glycosylated; and incubating the native substantially pure N-terminal fragment obtained in step (5) of the process described above with carboxypeptidase Y, thus confirming the presence of glutamine at the carboxy-terminal position 76 as also indicated by the sequence determination of the fragment CNBr-III.

DESCRIPTION OF DRAWINGS

The results of the above purification and characterization procedures are shown in FIGS. 1–9, wherein:

FIG. 1A also shows the results of quantitative radioimmunoassay of the individual fractions obtained as above, using an antibody raised against a porcine homolog of the above human N-terminal fragment.

DETAILS OF THE INVENTION

Figure 1A:
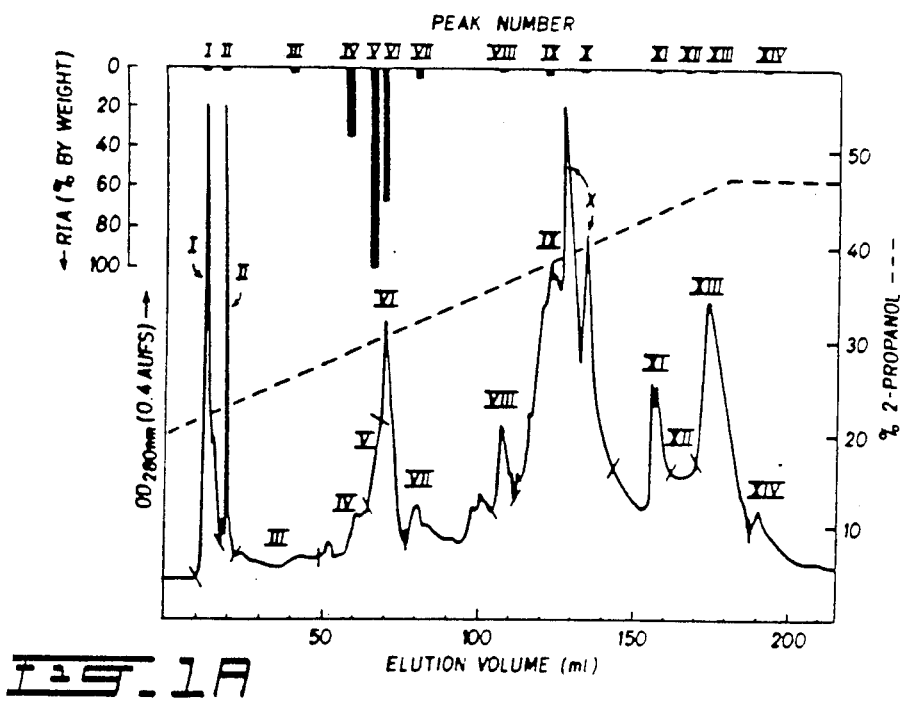
FIG. 1A shows the results of HPLC on a column of octadecylsilane (ODS) supported on glass beads of 5 micron diameter (5-Micron Ultrasphere ODS ®, (Beckman Instruments, Palo Alto, Calif.) of the material not retained on CMC obtained from step (4) of the process described above, using 0.02M triethylammonium formate (TEAF) at pH 3.0 as the aqueous buffer and a linear gradient (broken line) of 2-propanol as the organic eluant.
Figure 1B:
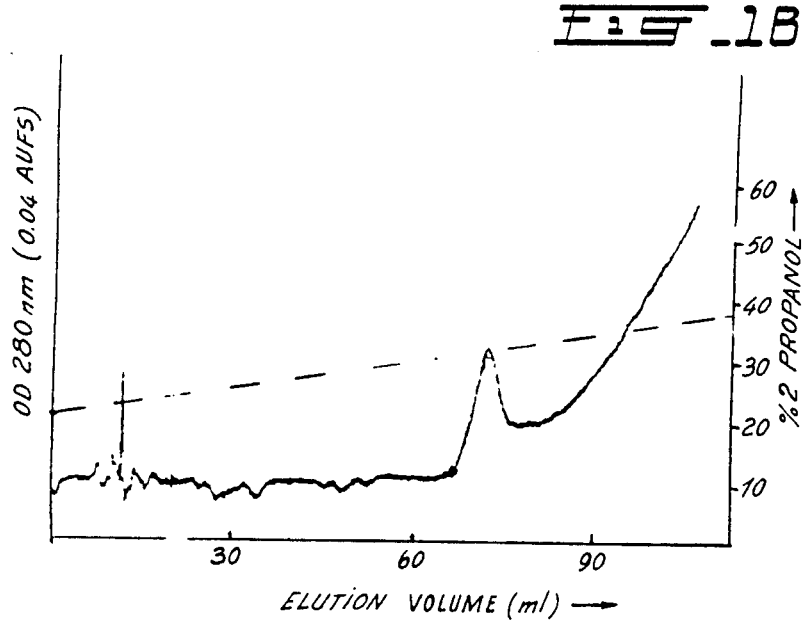
FIG. 1B shows the homogeneity of the N-terminal fragment of human pro-opiomelanocortin, viz., the glycopeptide of this invention, upon HPLC of the combined peaks V and VI obtained as shown in FIG. 1A, on a Micro-Bondapak C-18 ® column (Waters Associates, Milford, Mass.) and under the same conditions as described for FIG. 1A.

Isolation and Purification of the N-Terminal Fragment of Human Pro-Opiomelanocortin The process of preparing the N-terminal fragment of human pro-opiomelanocortin, viz., the glycopeptide of this invention, comprises the following steps in the sequence listed below:

(1) Extraction of fresh or frozen human pituitaries with HCl/acetone;

(2) Precipitation of the extract with NaCl, preferably in two successive stages, to obtain a precipitate;

(3) Dialyzing said precipitate against distilled water and freeze-drying the non-dialyzeable portion thereof, or preferably suspending said precipitate in water, adjusting to pH 3.0 followed by ultrafiltration against distilled water, preferably on a membrane having a cut-off point at a molecular weight of about 500, and freeze-drying the portion retained on the ultrafilter;

(4) Purifying one or the other of said last-named portions by chromatography on carboxymethylcellulose (CMC) in the manner described by Chrétien et al., Biochem. Biophys, Res. Commun. (1976) 72, 472, using an ammonium acetate gradient (0.1–1.0M), and collecting the material not retained on CMC in the first eluates;

(5) Said last-named eluates i.e. the material which is not retained on CMC, is further purified by HPLC on a column of a suitable adsorbent such as an alkylsilane supported on glass beads, preferably on a column of 5-Micron Utrasphere ODS ® (Beckman Instruments, Palo Alto, Calif.) using a suitable liquid chromatograph equipped with a U.V. detector, preferably a Waters Model 204 liquid chromatograph equipped with a Model 450 variable wavelength U.V. detector (both from Waters Associates, Milford, Mass.). A volatile buffer such as an alkylamine formate, preferably 0.02M triethylammonium formate (TEAF) at pH 3.0 is used as the aqueous buffer and a linear gradient of a water-miscible lower alkanol, preferably 2-propanol, from 20 to 47 percent by volume, is used as the organic eluant in the manner described by Seidah et al., (1980) J. Chromatogr. 193, 291, or by Seidah et al. (1980) Analytical Biochem. 109, 185–191. Optical density of the eluates is monitored at a suitable wavelength, preferably at 280 nm, and individual fractions are collected and freeze-dried. Weighed portions of the solids obtained in this manner are subjected to quantitative radioimmunoassay (RIA), using an antibody of porcine origin raised against the porcine N-terminal fragment as described by Lariviere et al., cited above. FIG. 1A shows that the major part of the human N-terminal fragment as recognized by the above RIA is eluted under the above conditions in peaks V and VI at ratios by volume of 2-propanol;

TEAF of about 29:71 to 32:68. The material from the above two peaks is combined and a sample thereof is subjected to the same HPLC procedure as above, to yield the glycopeptide of this invention, viz., the N-terminal fragment of human pro-opiomelanocortin in the substantially pure state. The homogeneity of said glycopeptide is shown in FIG. 1B, and is further demonstrated by eletrophoresis on SDS polyacrylamide in the manner described by Benjannet et al. (1980) and Seidah et al., (1980), both cited above, which shows that the above glycopeptide migrates as a single band with an apparent molecular weight of about 16000 to about 18000. The process is illustrated in the following flow-sheet I.

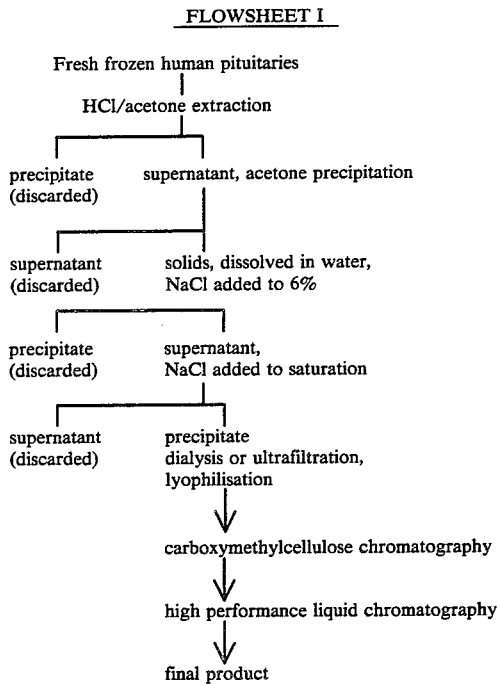

Characterization of the N-Terminal Fragment of Human Pro-Opiomelanocortin by Chemical Structure Briefly, determination of the amino acid sequence of the reduced and carboxymethylated glycopeptide establishes the sequence of amino acid residues 1–52, with exception of the residue in position 50; the structure of this part of the molecule is further confirmed by localization of the cysteine residues and by amino acid analysis, both carried out on the native glycopeptide. Treatment of the native glycopeptide with cyanogen bromide followed by HPLC gives three fragments designated as CNBr-I, CNBr-II, and CNBr-III, respectively; the structures of CNBr-II and CNBr-III are established by amino acid analysis and by sequencing as comprising residues 35–53 for CNBr-II, thus establishing lysine in position 50 and methionine in position 53, and residues 54–76 for CNBr-III, with glutamine in position 76, at the C-terminus. Glutamine as the C-terminal residue of the glycopeptide is also confirmed by carboxypeptidase-Y digestion of the reduced and carboxymethylated glycopeptide, thus establishing the length of its chain unambiguously as having 76 amino acid residues. Digestion of the fragment CNBr-I with staphylococcal protease V8 followed by HPLC gives three fractions, and amino acid analysis of the latter establishes their respective compositions which permit the localization of disulfide bridges between the cysteine residues at positions 2 and 8, and at positions 20 and 24. Finally, glycosylation sites are identified at the threonine residue in position 45 and at the asparagine residue in position 65. Details of the above procedure are as follows:

(a) Localization of Cysteine Residues

The incorporation of $^{14}C$-iodoacetamide into the glycopeptide of this invention is advantageously carried out in the manner described by Crestfield et al., in J. Biol. Chem. 238, 622 (1963). It is noted that incorporation of $^{14}C$-iodoacetamide does not occur in the absence of a reducing agent, not even under forced conditions, and this is interpreted as meaning that the cysteine residues are linked by disulfide bridges, see below. However, incorporation of $^{14}C$-iodoacetamide proceeds smoothly in the presence of a reducing agent, preferably dithiothreitol, to give the correspondingly labelled glycopeptide. The amino acid sequence of the latter is established by microsequencing on a commercially available sequenator, using appropriate buffers, reagents, and washes in a suitable program and suitable carriers. The preferred sequenator is an updated Beckman ® Model 890B sequenator (Beckman Instruments, Palo Alto, Calif.) equipped with a Sequemat ® Model P-6 auto-converter (Sequemat Inc., Watertown, Mass.) using the Edman procedure; the preferred buffer is 0.3M Quadrol ® at pH 9.0, and the preferred carriers are sperm whale apomyoglobin and 1,5-dimethyl-1,5-diaza-undecamethylene polymethobromide (Polybrene ®, Aldrich Chemical Co., Milwaukee, Wis.). The program and procedure are similar to those described by Crine et al. (1978), Chrétien et al. (1979), and Seidah et al. (1978), all cited above. The thiazolinones collected from each sequenator cycle are mounted on a suitable counter, preferably a Beckman ® liquid scintillation counter using a toluene-based scintillation cocktail, preferably Aquasol ® (New England Nuclear, Lachine, Quebec, Canada). The results shown in FIG. 2 indicate cysteine residues at positions 2, 8, 20, and 24, and it is noted that about 30% of the molecules of the above glycopeptide lack the first N-terminal residue, thus giving rise to a partial sequence with cysteine residues in positions 1, 7, 19 and 23.

(b) Amino Acid Analysis

Samples of the reduced and carboxymethylated glycopeptide of this invention are hydrolyzed with 5.7M HCl at 105° C. for 24, 48 and 72 hours in evacuated sealed tubes and the amino acid compositions of the respective hydrolysates are determined using a modified Beckman ® Model 120 C amino acid analyzer equipped with a Model 126 computing integrator. Separation of the amino acids is effected using Beckman ® W-3 resin which permits the separation of all amino acids and of the hexosamines in the manner described by Fauconnet et al. (1978) Anal. Biochem. 91, 403–409. The results of a typical experiment are shown in Table 1 which includes, for purposes of comparison, the amino acid analysis of a glycosylated peptide isolated from human pituitaries as described by Estevariz et al. cited above and designated as DEAE-II. It is apparent from Table 1 that DEAE-II and the glycopeptide of this invention are not identical. Table 1 also shows that glucosamine and galactosamine can be detected after 24 hours hydrolysis but that they are destroyed by 48 hours and 72 hours hydrolysis.

TABLE 1

| Amino Acid | 24 hrs | 48 hrs | 72 hrs | Integer | DEAE II |
|---|---|---|---|---|---|
| Asx | 8.07 | 8.21 | 7.95 | 8 | 8.7 |
| Thr | 3.73 | 3.54 | 3.50 | $4^2$ | 4.1 |
| Ser | 9.10 | 8.56 | 8.16 | $10^2$ | 7.6 |
| Glx | 10.16 | 9.79 | 9.68 | 10 | 9.8 |
| Pro | 5.04 | 4.72 | 5.25 | 5 | 5.0 |
| Gly | 6.90 | 7.31 | 7.20 | 7 | 8.0 |
| Ala | 3.03 | 3.21 | 3.10 | 3 | 5.3 |
| Cys | 3.20 | 3.64 | 3.54 | $4^3$ | 3.9 |
| Val | 1.33 | 0.90 | 1.05 | 1 | 3.2 |
| Met | 1.78 | 1.60 | 1.07 | 2 | 2.1 |
| Ile | 0.70 | 0.95 | 0.90 | 1 | 1.3 |
| Leu | 6.00 | 6.10 | 6.10 | 6 | 6.4 |
| Tyr | 0.75 | 1.01 | 1.02 | 1 | 1.1 |
| Phe | 2.50 | 2.63 | 2.85 | 3 | 3.0 |
| His | 1.12 | 0.98 | 1.00 | 1 | 1.8 |
| Lys | 2.28 | 2.36 | 2.38 | 2 | 4.1 |
| Trp | n.d. | n.d. | n.d. | $2^1$ | 1.6 |
| Arg | 5.98 | 6.36 | 6.05 | 6 | 5.0 |
| GlcN | +++ | | | +++ | |
| GalN | + | | | + | |
| Presumed Total | | | | 76 | 82 |

[1] Confirmed by sequence
[2] Corrected for destruction during hydrolysis (10-15%)
[3] Determined as S-carboxymethyl cysteine.
n.d. = Could not be determined due to destruction upon hydrolysis
GlcN, GalN = glucosamine and galactosamine, respectively (c) Determination of Amino acid Sequence A sample of the reduced and carboxymethylated glycopeptide of this invention is subjected to sequence determination on an updated Beckman ® model 890 B sequenator using the Edman procedure and 0.3M Quadrol ® at pH 9.0 as the sequencer buffer with Polybrene ® in the sequenator cup and using Beckman's 0.1M Quadrol ® program with $S_1+S_2$ was No. 12.11.78. The sequenator is equipped with a Sequemat ® Model P-6 autoconverter so that all conversions are done automatically immediately following the cleavage step using 1.5M HCl in methanol at 65° C. The phenylthiohydantoin (PTH) derivatives of the amino acids are separated on a column of octadecylsilane (ODS) supported on glass beads of 5 micron diameter (5 Micron Ultrasphere ODS ®, Beckman) in the manner described by Somack (1980) Anal. Biochem. 104, 464-468, except that the PTH derivatives of glutamic and aspartic acids and S-carboxymethyl cysteine are detected as their respective methyl esters and that PTH-norleucine is added as an internal standard. Separations are effected on a Waters ® Model 204 liquid chromatograph equipped with a WISP ® Model 710 auto-injector and a Data Module 730 integrator-plotter and Model 720 system controller (all from Waters Associates, Milford, Mass.)

Figure 3:
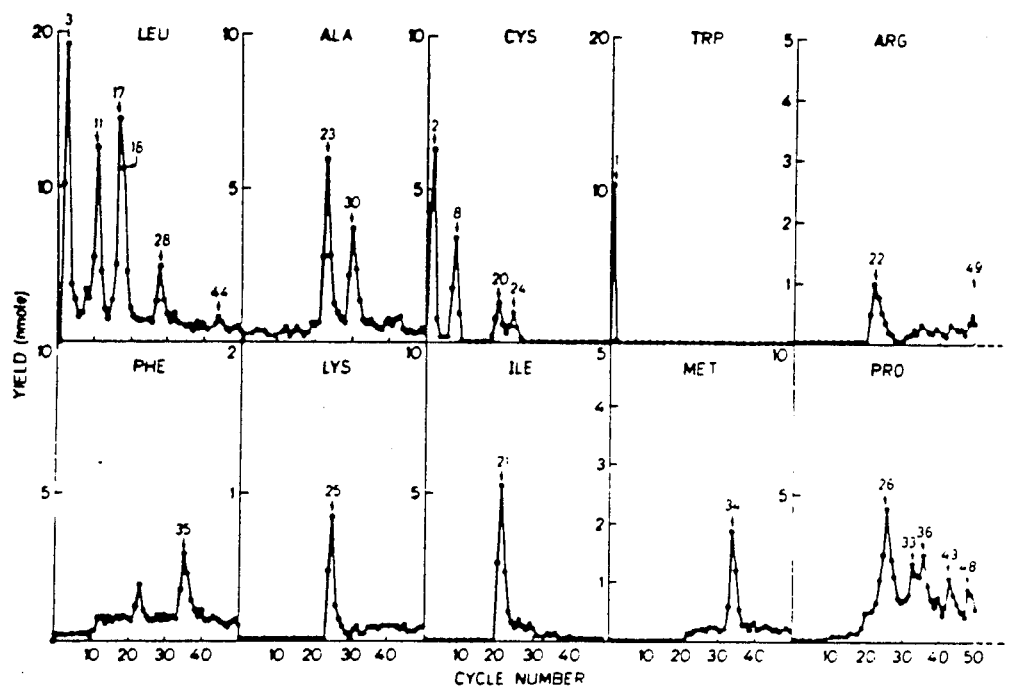
FIG. 3 shows the yields of the phenylthiohydantoin derivatives of the individual amino acids isolated in the sequence determination of the reduced and carboxymethylated substantially pure N-terminal fragment of human pro-opiomelanocortin, as a function of sequenator cycle number; the numbers above the individual peaks indicate the position assigned to the respective residue along the amino acid chain of the above N-terminal fragment.
Figure 3:
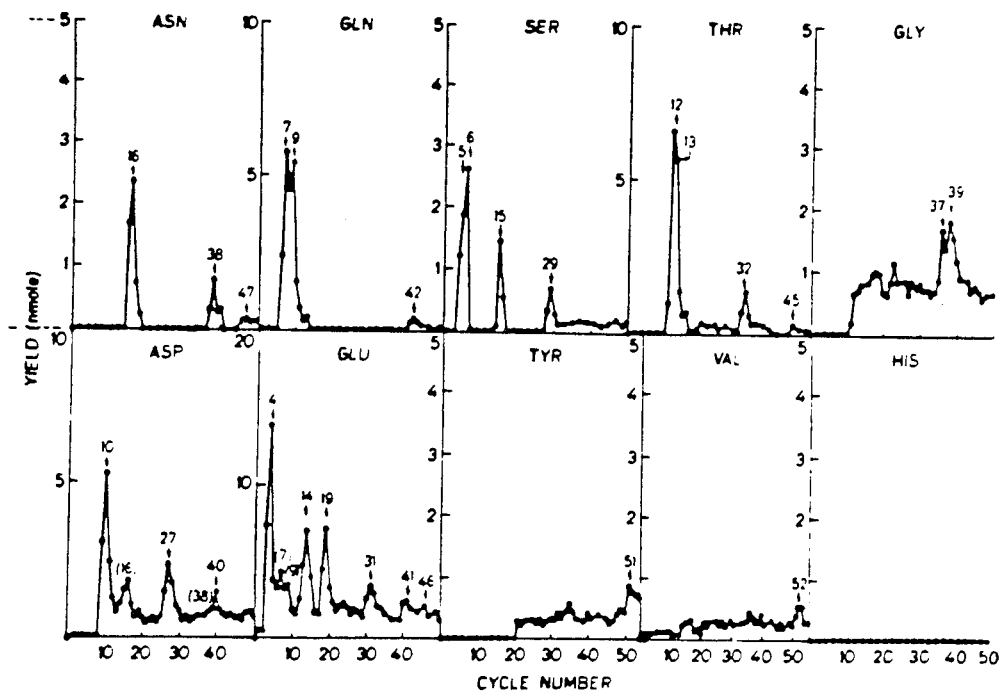

Results of a typical experiment are shown in FIG. 3, and it is apparent that only the first 52 amino acid residues are positively identified, with exception of residue 50 (see below), although the above sequence determination was extended to 60 cycles.

(d) Cyanogen Bromide Cleavage and Identification of Cleavage Products

Figure 4:
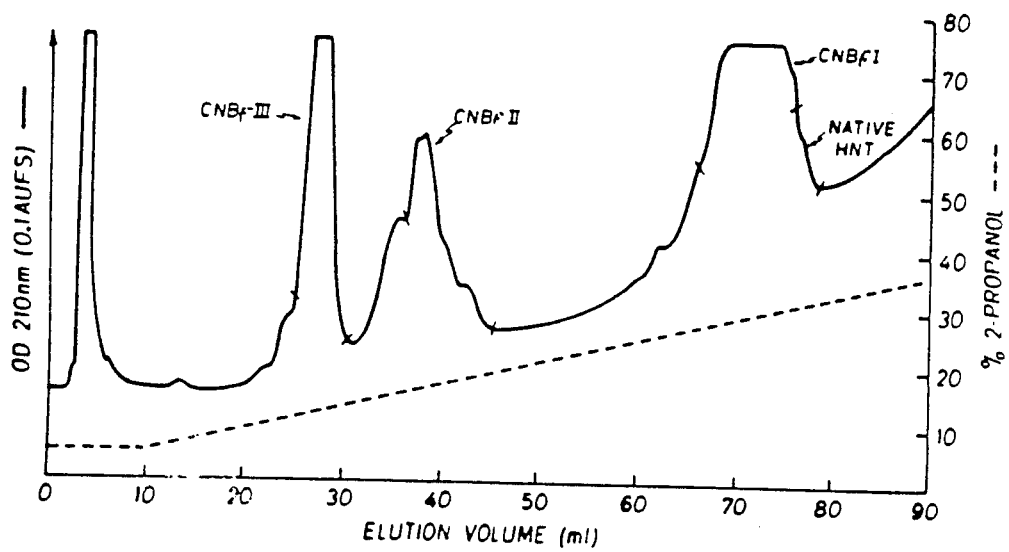
FIG. 4 shows the results of HPLC purification of the fragments obtained by CNBr cleavage of the native glycopeptide of this invention, using 0.02M triethylammonium phosphate (TEAP) as the aqueous buffer at pH 3.0 and a linear gradient of 2-propanol as the eluant (broken line). Eluates are separated by monitoring optical density at 210 nm.

The natine glycopeptide of this invention is treated with a molar excess of cyanogen bromide, preferably with a molar excess in the range of 1000, and the resulting mixture is separated by HPLC on a column of octadecylsilane supported on microporous glass beads, preferably on a Micro-Bondapak C-18 ® column (Waters Associates, Milford, Mass.) using triethylammonium phosphate as the aqueous buffer at pH 3.0 and a linear gradient of 2-propanol as the eluant to give three fragments designated as CNBr-I, CNBr-II and CNBr-III, see FIG. 4. Those three fragments are separated and each of them is further purified by HPLC under the same conditions as above except that a volatile buffer such as triethylammonium formate is used as the aqueous buffer, to give the fragments CNBr-I, CNBr-II, and CNBr-III as substantially pure compounds. Amino acid analysis is then performed on the above three fragments following 24 hours hydrolysis under the same conditions as described above under (b), and the sequences of amino acids in fragments CNBr-II and CNBr-III are determined as described above under (c).

Figure 5:
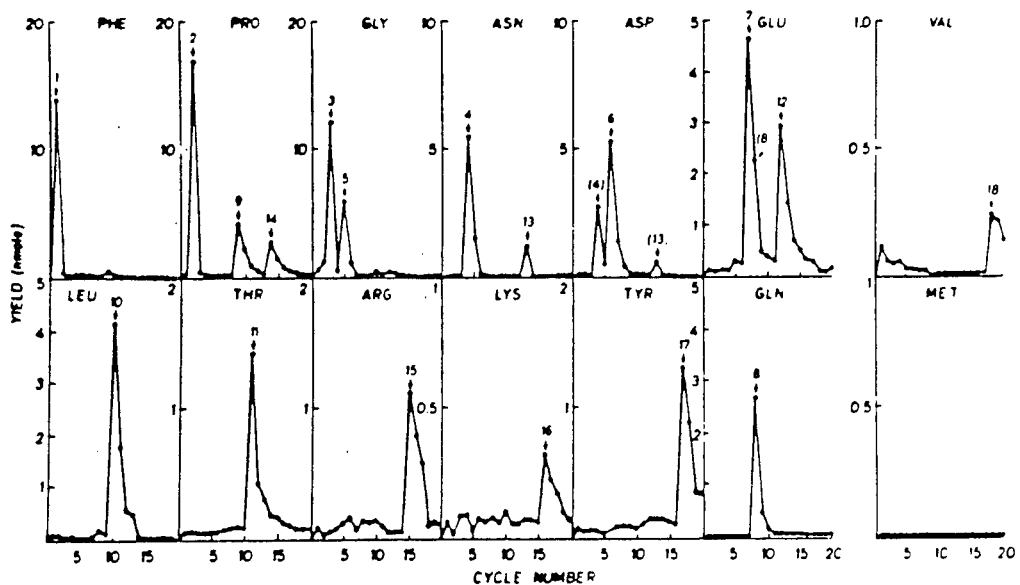
FIG. 5 shows the yields of the phenylthiohydantoin derivatives of individual amino acids isolated in the sequence determination of the purified fragment CNBr-II as a function of sequenator cycle number; the numbers above the individual peaks indicate the position assigned to the respective residue along the amino acid chain of the fragment CNBr-II.
Figure 6:
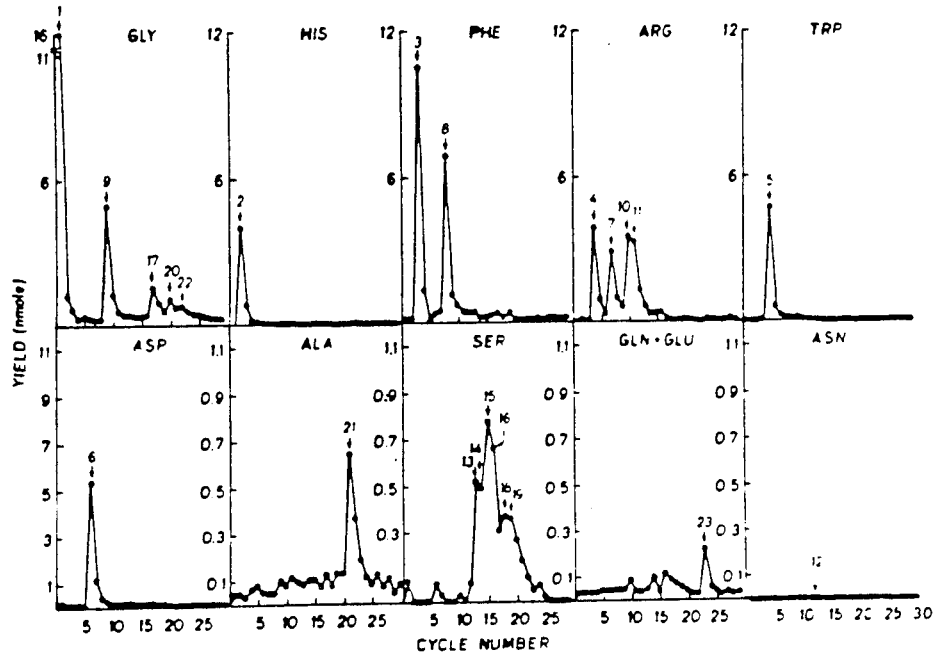
FIG. 6 shows the yields of the phenylthiohydantoin derivatives of the individual amino acids isolated in the sequence determination of the purified fragment CNBr-III as a function of sequenator cycle number; the numbers above the individual peaks indicate the position assigned to the respective residue along the amino acid chain of the fragment CNBr-III.

The results of one typical experiment are shown in FIGS. 4, 5, and 6, and in Table 2. FIG. 4 shows the cleavage of the native glycopeptide into the three fragments CNBr-I, -II, and -III, and Table 2 gives the results of the amino acid analyses of the above three fragments; FIGS. 5 and 6 show the results of the sequence determinations of the fragments CNBr-II and CNBr-III, respectively.

The sequence determination (60 cycles) of the reduced and carboxymethylated glycopeptide described above under (c) and shown in FIG. 3 had established the positions of the residues 1-52, with exception of the residue in position 50, and had also established a methionine residue in position 34. It is known in the art that cyanogen bromide cleaves peptides at methionine residues with concomitant conversion of carboxy-terminal methionine to mixtures of homoserine and homoserine lactone. The amino acid analysis of the fragment CNBr-I shown in Table 2 corresponds to the composition of the fragment of the glycopeptide containing residues 1-34, including the methionine residue at position 34 which is detected as a mixture of homoserine and homoserine lactone, thus establishing the structure of the fragment CNBr-I and confirming the structure of the glycopeptide with regard to amino acid residues 1-34.

The sequence determination (20 cycles) of the fragment CNBr-II shown in FIG. 5 establishes the nature and the positions of residues 35-52 of the glycopeptide, identical with results obtained by sequencing the glycopeptide (see FIG. 3) except that the residue in position 50 is now established as being lysine. The amino acid analysis of the fragment CNBr-II shown in Table 2 corresponds to the composition of residues 35-52 and establishes in addition the presence of methionine at the C-terminus of that fragment, detected as a mixture of homoserine and homoserine lactone, which permits the unambiguous assignment of methionine to position 53.

The sequence determination (30 cycles) of the fragment CNBr-III shown in FIG. 6 demonstrates the nature and the positions of 22 of the 23 amino acid residues in that fragment and identifies glutamine as the C-terminal residue in cycle 23, as no other residues are identifiable beyond cycle 23. The fact that glutamine is indeed the C-terminal residue not only of the fragment CNBr-III but also of the complete glycopeptide is confirmed by digestion of the latter with carboxypeptidase-Y, see below. However, FIG. 6 shows an unidentifiable residue in cycle 12 (corresponding to position 65 of the glycopeptide) and the amino acid analysis of the fragment CNBr-III shown in Table 2 accounts for all of the 22 residues identified by sequencing except for one residue Asx which in this case can only be asparagine in position 65, presumably not identifiable as such because it is glycosylated, as will be discussed below.

The above results of the sequence determinations of the fragments CNBr-II and CNBr-III together with the sequence determination of the reduced and carboxymethylated glycopeptide shown in FIG. 3 establish the length of the chain of the glycopeptide of this invention as being composed of 76 amino acid residues, in perfect agreement with the presumed total shown in Table 2. That latter Table also confirms the presence of glucosamine and of galactosamine previously noted in Table 1, and establishes that the two hexosamines are present in fragment CNBr-II at a ratio of about 1:2, and in fragment CNBr-III at a ratio of about 3:1. The significance of those results is discussed below.

TABLE 2

| Amino Acids | CNBr-I (residues 1–34) | CNBr-II (residues 35–53) | CNBr-III (residues 54–76) |
|---|---|---|---|
| Asx | 3.10(3) | 2.93(3) | 2.50(2) |
| Thr | 2.94(3) | 0.99(1) | — |
| Ser | 3.65(4) | — | 5.81(6) |
| Glx | 6.21(6) | 3.23(3) | 1.15(1) |
| Pro | 1.78(2) | 3.17(3) | — |
| Gly | — | 2.25(2) | 4.93(5) |
| Ala | 2.39(2) | — | 0.97(1) |
| Cys | n.d.(4) | — | — |
| Val | — | 1.11(1) | — |
| Met | +(1)[1] | +(1)[1] | — |
| Ile | 0.88(1) | — | — |
| Leu | 4.95(5) | 1.06(1) | — |
| Tyr | — | 0.92(1) | — |
| Phe | — | 1.04(1) | 2.00(2) |
| His | — | — | 1.01(1) |
| Lys | 1.24(1) | 0.67(1) | — |
| Trp | n.d.(1)[2] | — | 1.43(1) |
| Arg | 0.95(1) | 1.36(1) | 3.93(4) |
| GlcN | — | 0.46 | 0.83 |
| GalN | — | 0.85 | 0.35 |
| Presumed Total | 34 | 19 | 23 |

[1]Determined as presence of homoserine and homoserine lactone
[2]In this peptide the Trp was completely destroyed upon hydrolysis
n.d. = Not determined but confirmed by sequence
Numbers in parentheses indicate the nearest integers (e) Carboxypeptidase-Y Digestion The reduced and carboxymethylated glycopeptide of this invention is incubated in a buffer at pH 5.5 and at 37° C. with 1 percent (wt/wt) of carboxypeptidase-Y (Boehringer-Mannheim). Aliquots of the mixture are removed at stated intervals, heated to 100° C. for 5 minutes to inactive the enzyme, and freeze-dried. Amino acid analysis of the above samples shows that glutamine in position 76 is the carboxy-terminal residue, thus confirming the results of the sequence determination of the fragment CNBr-III, see FIG. 6, in which glutamine and/or glutamic acid had been found in cycle 23. That latter result also confirms the length of the chain of the N-terminal fragment of human pro-opiomelanocortin, viz, of the glycopeptide of this invention, as being composed of 76 amino acid residues.

(f) Digestion of Fragment CNBr-I with Staphylococcal Protease V8 and Localization of Disulfide Bridges As discussed above under (a), the fact that incorporation of $^{14}$C-iodoacetamide does not take place in the absence of a reducing agent indicates that the cysteine residues in the glycopeptide of this invetion are linked by disulfide bridges. Three different locations for such disulfide bridges are theoretically possible, viz., between the cysteine residues (i) at positions 2 and 8, and at positions 20 and 24; (ii) at position 2 and 20, and at positions 8 and 24; and (iii), at positions 2 and 24, and at positions 8 and 20. Differentiation between those three possibilites is effected by the use of an endopeptidase which is specific for peptide bonds involving glutamic acid residues, because the latter residues are present in the glycopeptide of this invention, inter alia at the strategic positions 4, 14, 19, and 31. Moreover, as all the cysteine residues are located in the fragment CNBr-I the structure of which is known from the direct sequencing of the glycopeptide, see FIG. 3, it is more advantageous to use that latter fragment for the purpose of localization of the disulfide bridges rather than the glycopeptide itself.

Figure 9:
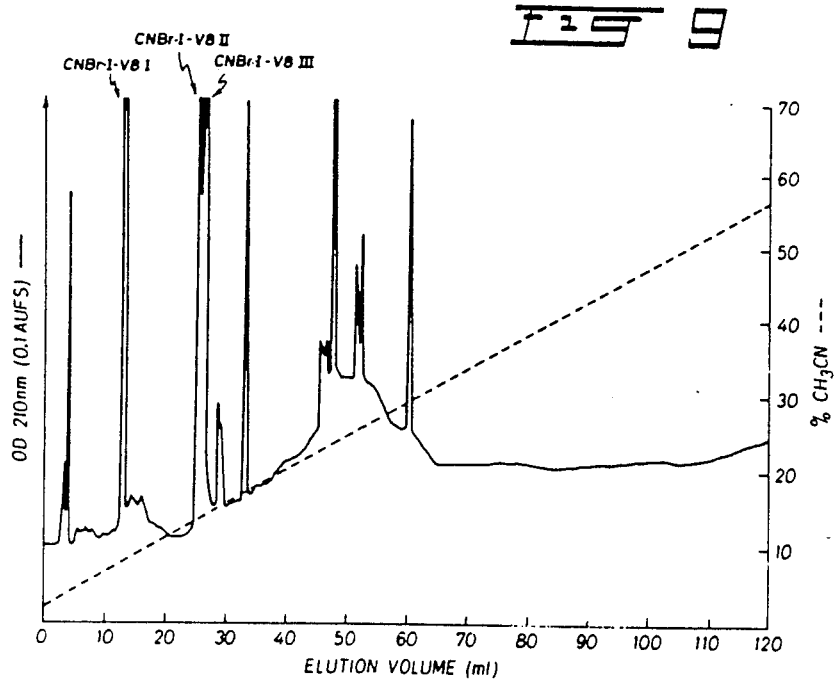
FIG. 9 shows the results of HPLC purification of the fractions CNBr-I-V8-I, CNBr-I-V8-II, and CNBr-I-V8-III obtained by treatment of the fragment CNBr-I with staphylococcal protease V8.

The native substantially pure fragment CNBr-I obtained as described in section (d) is incubated with about 5 percent (wt/wt) of staphylococcal protease V8 (obtained from Dr. G. Drapeau, Université de Montréal, Montreal, Canada) at 37° C. in solution in 0.05M aqueous sodium bicarbonate at pH 7.9 for 24 hours in the manner described by Houmard et al. cited above. The mixture is freeze-dried and separated by HPLC on a column of octadecylsilane supported on microporous glass beads, preferably on Micro-Bondapak C-18® (Waters Associates, Milford, Mass.), using 0.02M triethylammonium phosphate at pH 3.0 as the aqueous buffer and a linear gradient of acetonitrile, from 2 percent to 58 percent, as the organic eluant, see FIG. 9. Three distinct fractions, designated as CNBr-I-V8-I, CNBr-I-V8-II and CNBr-I-V8-III are thus obtained, purified individually by HPLC under the same conditions as above, freeze-dried, hydrolyzed in 5.7M HCl in evacuated tubes at 105° C. for 24 hours, and their compositions determined by amino acid analysis as described above. The results of one typical experiment are shown in Table 3. It is seen that the above enzyme cleaved the fragment CNBr-I at the glutamic acid residues in positions 14 and 19, to give fraction CNBr-I-V8-I containing the residues 1–14, fraction CNBr-I-V8-II containing the residues 15–19, and fraction CNBr-I-V8-III containing the residues 20–34. This result is only compatible with the location of disulfide bridges between the cysteine residues at positions 2 and 8, and at positions 20 and 24, as described above as alternative (i); in the other two alternatives (ii) and (iii) the cysteine residues in fraction CNBr-I-V8-I would have been attached by disulfide bridges to the cysteine residues in fraction CNBr-I-V8-III, and neither of those fractions would have been obtained as a separate entity following digestion of the fragment CNBr-I with staphylococcal protease V8. The location of the disulfide bridges between cysteine residues at positions 2 and 8, and at positions 20 and 24, is shown in formula I, see below.

TABLE 3

| Amino Acids | CNBr-I-V8-I (residues 1–14) | CNBr-I-V8-II (residues 15–19) | CNBr-I-V8-III (residues 20–34) |
|---|---|---|---|
| Asx | 1.49(1) | 1.13(1) | 0.97(1) |
| Thr | 2.29(2) | — | 0.90(1) |
| Ser | 2.31(2) | 1.03(1) | 0.94(1) |
| Glx | 3.66(4)[1] | 0.52(1) | 0.82(1)[1] |
| Pro | — | — | 2.40(2) |
| Gly | — | — | — |
| Ala | — | — | 1.91(2) |
| Cys | n.d.(2) | — | n.d.(2) |
| Val | — | — | — |
| Met | — | — | +(1)[2] |
| Ile | — | — | 0.78(1) |
| Leu | 1.44(2)[1] | 2.47(2) | 1.12(1) |
| Tyr | — | — | — |
| Phe | — | — | — |
| His | — | — | — |
| Lys | — | — | 0.84(1) |
| Trp | n.d.(1) | — | — |
| Arg | — | — | 0.88(1) |
| Presumed | 14 | 5 | 15 |

TABLE 3-continued

| Amino Acids | CNBr-I-V8-I (residues 1-14) | CNBr-I-V8-II (residues 15-19) | CNBr-I-V8-III (residues 20-34) |
|---|---|---|---|
| Total | | | |

[1] The Glu or Leu values were low, but their amount and presence were confirmed by sequence (FIGS. 3 and 7).
[2] Detected as homoserine (lactone)
n.d.= not determined due to destruction upon hydrolysis, but confirmed by sequence (FIGS. 3 and 7)
Numbers in parentheses indicate the nearest integers (g) Glycosylation Sites, and Nature of Glycosidic Linkages As discussed above under (d) and as shown in Table 2, the fragments CNBr-II and CNBr-III contain glucosamine and galactosamine in ratios of about 1:2 and of about 3:1, respectively, even though the values shown in Table 2 are not corrected for hydrolysis and might possibly be higher.

Concerning the fragment CNBr-III, the amino acid analysis shown in Table 2 establishes the presence of two Asx residues, only one of which is accounted for by sequence determination as aspartic acid in position 59 while a non-identifiable residue is found in cycle 12 of the sequence determination which corresponds to position 65, see FIG. 6. With all other amino acid residues determined by amino acid analysis being accounted for by the above sequence determination, the missing Asx residue can only be asparagine in position 65. The impossibility of identifying that latter residue in the sequence determination of the fragment CNBr-III is due to the fact that it represents a glycosylated asparagine, as the phenylthiohydantoin derivative of the latter is not soluble in butyl chloride which is the solvent used for extraction of phenylthiohydantoin derivatives in the accepted sequencing procedure, see Seidah et al. (1981) Biochem. Biophys. Res. Comm. 100, 901. Furthermore, the facts that the fragment CNBr-III contains glucoasmine and galactosamine in a ratio of about 3:1 and that the glycosylation site at asparagine in position 65 is associated with the triad Asn 65-X-Ser 67 are in agreement with an N-glycosidic linkage at that position, in conformity with the general rules on glycosylation established by analogy with other glycosylated peptides, see Seidah et al. (1981) cited above, Kornfeld et al. (1976) Ann. Rev. Biochem. 45, 217-238, and Pless et al. (1977) Proc. Natl. Acad. Sci. USA 74, 134-136. Another factor in favour of an N-glycosidic linkage at asparagine in position 65 is the comparative stability of that linkage, which appears to remain unaffected by the conditions used in the sequencing procedure.

Concerning the fragment CNBr-II, both the ratio of glucosamine to galactosamine of about 1:2 and the absence in that fragment of the triad Asn-X-Ser or Asn-X-Thr which is characteristic for N-glycosidic linkages are cogent arguments against the presence of an N-glycosylation site in the fragment CNBr-II. The presence of an O-glycosylation site is the only other alternative, and the only location available for such a site in the fragment CNBr-II is the threonine residue at position 45, as no other threonine or serine or other hydroxylated residues are present in that latter fragment. Although no general rules for specific peptide sequences associated with O-glycosidic linkages have been established to date, it is known that this type of oligosaccharide linkage is usually found in a proline-rich region, and usually contains galactosamine as the major hexosamine, see Li et al. (1978) J. Biol. Chem. 253, 7762-7770. Both of those conditions are met in this case: there are proline residues in positions 36, 43, and 48 of the fragment CNBr-II, and it contains about twice as much galactosamine than glucosamine. It is therefore concluded that threonine in position 45 is O-glycosylated. The fact that threonine at position 45 is actually identified in the sequence determination of the reduced and carboxymethylated glycopeptides, see FIG. 3, and in the sequence determination of the native fragment CNBr-II (see FIG. 5, cycle 11 corresponds to position 45), is explained by the lability of the O-glycosidic linkage under mildly alkaline conditions, see Anderson et al. (1964), J. Biol. Chem. 239, PC2716, as the sequencing procedure is carried out at pH 9 and at 58° C.

Figure 7:
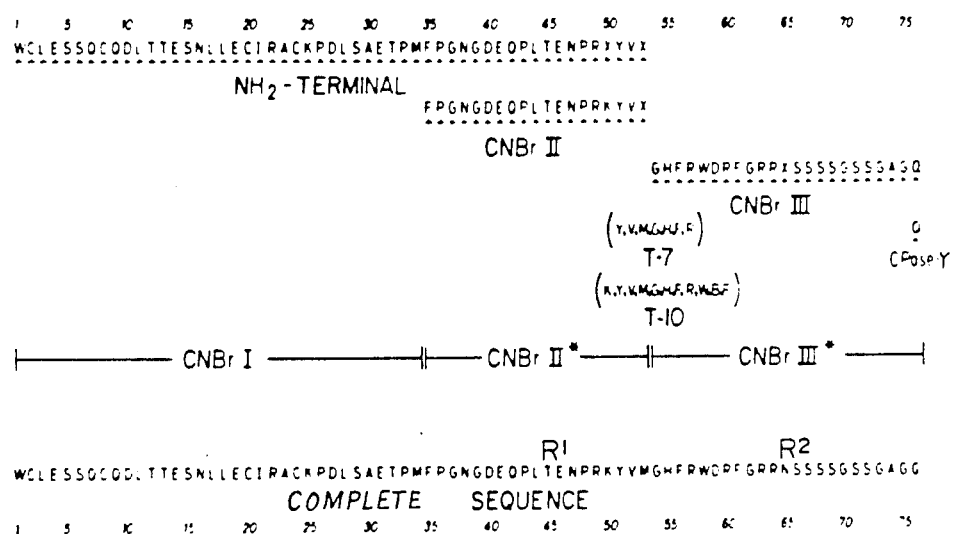
FIG. 7 shows the alignment of the sequences determined for the reduced and carboxymethylated N-terminal fragment, see FIG. 3, residues 1–52; of the fragment CNBr-II, see FIG. 5, residues 35–52; and of the fragment CNBrIII, see FIG. 6, residues 54–76; comparison of the amino acid compositions of the tryptic digest fractions T-7 and T-10 obtained by Seidah et al. (1980) cited above, with the region bridging the carboxy-terminal of fragment CNBr-II with the N-terminal of fragment CNBr-III, thus confirming the methionine residue in position 53; confirming the presence of lysine at position 50, see structure of CNBr-II; confirmation of the presence of glutamine at the carboxy-terminal in position 76 by carboxypeptidase-Y digestion of the native glycopeptide; confirming the structure of the fragment CNBr-I by the amino acid compositions of the fractions obtained by digestion thereof with staphylococcal protease V8, designated as CNBr-I-V8-I, CNBr-I-V8-II, and CNBr-I-V8-III, respectively; indicating the presnece of glycosylated residues in fragments CNBr-II and CNBr-III by means of asterisks; indicating the positions of the glycosyl moieties at threonine in position 45 and at asparagine in position 65 by the symbols $R^1$ and $R^2$, respectively; and showing the complete sequence of the glycopeptide of this invention.

The complete structure of the N-terminal fragment of human pro-opiomelanocortin, i.e. of the glycopeptide of this invention, is shown in the following formula I and in FIG. 7 in which the glycosyl moieties at threonine in position 45 and at asparagine in position 65 are indicated the symbols $R^1$ and $R^2$ respectively and the disulfide bridges are shown by the symbol ⌐⌐:

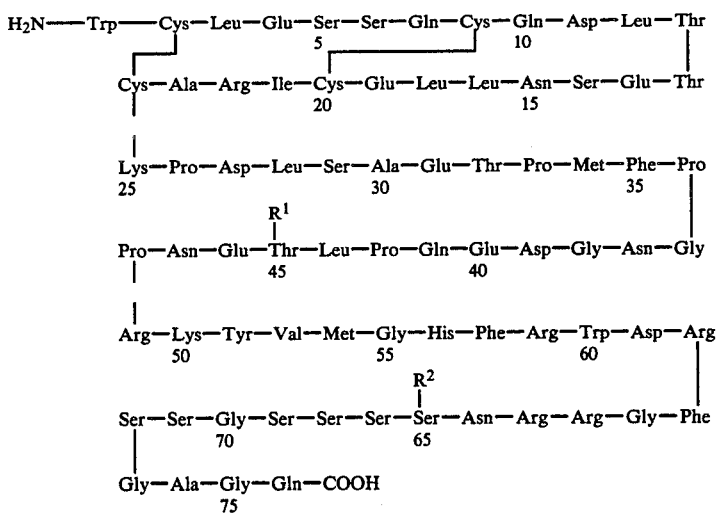

Figure 8:
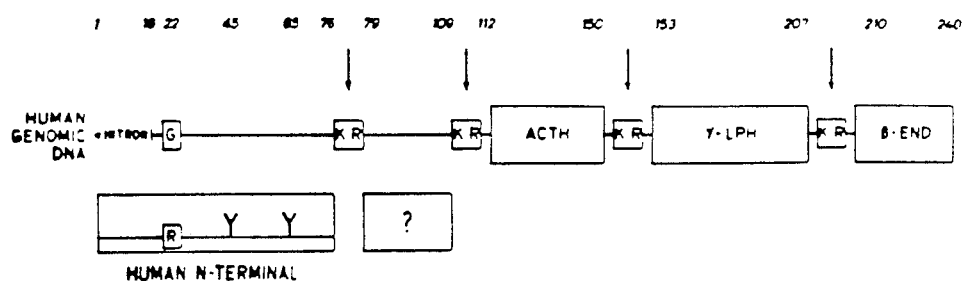
FIG. 8 shows a comparison of the reported genomic DNA sequence of human pro-opiomelanocortin with that obtained from the protein sequence of the isolated human N-terminal peptide. A predicted fragment from the DNA sequence comprising residues 79 to 109 has not yet been identified. It is apparent that only Lys-Arg residues are cleaved from this precursor molecule based on the known maturation end products. A vertical arrow indicates preferred cleavage sites, and the symbol Y indicates the glycosylation sites.

It is seen from the above formula I that the glycopeptide of this invention is different from the N-terminal fragment predicted from the genomic DNA structure shown by Chang et al. (1980) cited above. Apart from the fact that the length of the amino acid chain, the existence of disulfide bridges, and the presence of two glycosyl moieties were not predicted, the glycopeptide of this invention has an arginine residue in position 22, while the genomic structure had predicted a glycine residue in the same position, see FIG. 8. Furthermore, the sequence predicted from the genomic DNA did not include residues 1-19 because of the presence of an intron in those positions.

The glycopeptide of formula I is also different from the N-terminal fragment of pro-opiomelanocortin described by Seidah et al. (1980) cited above, in that the latter was stated to be composed of about 103 amino acid residues, with the sequence of residues 1-79 established by a combination of direct sequencing and of tryptic peptide mapping. Furthermore, the latter compound contains a glycine residue in position 66 which is not present in the glycopeptide of this invention, so that the amino acid residues 66-76 of the glycopeptide of formula I are different from those of the former and appear to be shifted by one unit to a lower positional number. In addition, the length of the amino acid chain of the glycopeptide of this invention is now precisely determined as 76 residues, with glutamine at the carboxy-terminus, and having two glycosyl moieties attached thereto while the compound described by Seidah et al. (1980) had only one such glycosyl group.

The glycopeptide formula I, viz., the N-terminal fragment of human pro-opiomelanocortin, potentiates the affects of ACTH upon steroidogenesis and stimulates the production of aldosterone by aldosteronoma cells. The above properties make it useful in the treatment of pathological conditions associated with diminished steroidogenesis or diminished secretion of aldosterone in mammals, especially in humans, and as a clinically useful tool for the diagnosis of aldosteronoma or of pituitary dysfunction. It is also present in the brain where it causes a number of behavioural changes related to normal and/or abnormal behaviour such as memory, mood, appetite, satiety, pain, sexual drive, and extreme sensitivity to noise, and it is thus useful in the treatment of pathological conditions associated with the above behavioural phenomena. The glycopeptide of formula I is also useful as a reagent for determining its own presence in biological fluids or tissues, by using it to raise specific antibodies thereto and then using said antibodies in an immunochemical assay of the glycopeptide.

The fact that the glycopeptide of this invention is of human origin is of particular advantage in the treatment of human patients suffering from the pathological conditions listed above. It has frequently been observed that species specificity is an important factor in hormonal therapy, and that hormones of human origin give the best results in the treatment of humans; for example, human growth hormone is the only acceptable hormone for the treatment of human dwarfism.

The influence of the glycopeptide of formula I upon ACTH and thus upon steriodogenesis, especially upon the production of corticosteroids and the release of corticosterone is conveniently measured in rat adrenal cortex suspensions by a modified version of the method described by Sayers in Ann. N.Y. Acad. Sci. 297, 220 (1977), with the modification consisting in using a sensitive radioimmunoassay for the various corticosteroids.

The stimulating effect of the glycopeptide of formula I upon the production of aldosterone is demonstrated in vitro by measuring the release of aldosterone from human aldosteronoma cells by means of the specific radioimmunoassay described by P. Vecesi in "Extrarenal Activity of Aldosterone and its Antogonists," p.72, W. Brendel, ed., Excerpta Medica, Amsterdam 1972. The results shown in Table 4 indicate that the N-terminal fragment of human pro-opiomelanocortin, viz., the glycopeptide of formula I, has about the same range of aldosterone-releasing activity as a homologous peptide prepared by Larivière et al., cited above, from pig pituitaries, and is about as active as synthetic ACTH 1-24.

TABLE 4

| Peptide | Concentration (M) | Aldosterone released, ng/$10^5$ cells ± SE |
|---|---|---|
| Control | — | 8.78 ± 0.45 (12)* |
| Pig N-terminal | 8.3 × $10^{-9}$ | 32.99 ± 2.29 (3) |
| | 8.3 × $10^{-8}$ | 32.24 ± 0.98 (3) |
| Human N-terminal | 8.3 × $10^{-9}$ | 27.21 ± 2.35 (3) |
| | 8.3 × $10^{-8}$ | 35.48 ± 4.43 (3) |
| ACTH 1-24 | 3.3 × $10^{-9}$ | 28.61 ± 2.54 (3) |
| | 3.3 × $10^{-8}$ | 33.18 ± 4.39 (3) |

*Figures in parentheses indicate the numbers of assays performed.

When the glycopeptide of formula I is employed in mammals, e.g. in mice, rats, or pigs, and especially in humans as an agent for regulating steroidogenesis, for stimulating the production of aldosterone or for regulating certain behavioural changes, or as a diagnostic tool it may be used alone or in combination with pharmaceutically acceptable carriers, the proportion of which is determined by the solubility and chemical nature of the compound, chosen route of administration and standard biological practice. For example, for parenteral administration by the intravenous, intramuscular, or subcutaneous routes the glycopeptide may be used in the form of a sterile solution or suspension in a pharmaceutically acceptable liquid carrier such as water, ethanol, propylene glycol, or polyethylene glycol, containing other solutes or suspending agents, for example enough saline or glucose to make the solution isotonic, bile salts, acacia, gelatin, sorbitan monoleate, polysorbate 80 (oleate esters of sorbitol and its anhydrides copolymerized with ethylene oxide), i.e. "Tween 80" ® and the like. Aqueous sterile solutions are preferred, and suitable preservatives, for example methyl or propyl p-hydroxybenzoate may be added as well as other solutes, for example sufficient sodium chloride or glucose to make the solution isotonic. The glycopeptide of this invention may also be administered intramuscularly in solutions or suspensions in sterile liquid carriers other than water, for example suitable vegetable or animal oils, with or without the use of other solutes or of suspending agents as listed above.

The dosage of the glycopeptide of formula I will vary with the form of administration and with the particular compound chosen. Furthermore, it wil vary with the particular host under treatment. Generally, treatment is initiated with small dosages substantially less than the optimum dose of the compound. Thereafter, the dosage is increased by small increments until the optimum effect under the circumstances is reached. In general, the glycopeptide of formula I is most desirably administered at a concentration level that will generally afford effective results in the regulation of steroidogensis by ACTH, in the regulation of aldosterone levels, and in the regulation of certain behavioural changes without causing any harmful or deleterious side effects and preferably at a level that is in a range of from about 0.1 mcg to about 500 mcg per kg body weight per day, although as aforementioned, variations will occur. However, a dosage level that is in the range of from about 0.1 mcg to about 100 mcg per kg per day, preferably in divided doses, is most desirably employed in order to achieve effective results.

When the glycopeptide of this invention is employed in human medicine, it is preferably administered systemically, either by intravenous, subcutaneous, or intramuscular injection, or by sublingual or nasal administration, in compositions in conjunction with a pharmaceutically acceptable vehicle or carrier.

For administration by the nasal route as drops or spray it is preferred to use the glycopeptide in solution in a sterile aqueous vehicle which may also contain other solutes such as buffers or preservatives, as well as sufficient quantities of pharmaceutically acceptable salts or of glucose to make the solution isotonic. Doses by the intranasal route range from 0.1 mcg to 250 mcg/kg/day or preferably about 0.1 mcg to about 100 mcg/kg/day.

The glycopeptide of this invention may also be amdinistred as nasal powders or insufflations. For such purposes the glycopeptide is administered in finely divided solid form together with a pharmaceutically acceptable solid carrier, for example a finely divided polyethylene glycol (Carbowax 1540 ®), finely divided lactose, or very finely divided silica (Cab-O-Sil ®). Such compositions may also contain other excipients in finely divided solid form such as preservatives, buffers, or surface active agents.

The glycopeptide of formula I may also be administered in one of the long-acting, slow-release or depot dosage forms described below, preferably by intramuscular injection or by implantation. Such dosage forms are designed to release from about 0.1 mcg to about 100 mcg per kilogram body weight per day.

It is often desirable to administer the glycopeptide continuously over prolonged periods of time in long-acting, slow-release, or depot dosage forms. Such dosage forms may either contain a pharmaceutically acceptable salt of the compound having a low degree of solubility in body fluids, for example salts with pamoic or tannic acid or carboxymethylcellulose, or they may contain the glycopeptide together with a protective carrier which prevents rapid release. In the latter case, for example, the glycopeptide may be formulated with a non-antigenic partially hydrolyzed gelatin in the form of a viscous liquid; or it may be absorbed on a pharmaceutically acceptable solid carrier, for example zinc hydroxide with or without protamine, and may be administered in suspension in a pharmaceutically acceptable liquid vehicle; or the glycopeptide may be formulated in gels or suspensions with a protective non-antigenic hydrocolloid, for example sodium carboxymethylcellulose, polyvinylpyrrolidone, sodium alginate, gelatine, polygalacturonic acids, for example, pectin, or certain mucopolysaccharides, together with aqueous or non-aqueous pharmaceutically acceptable liquid vehicles, preservatives, or surfactants. Examples of such formulations are found in standard pharmaceutical texts, e.g. in Remington's Pharmaceutical Sciences, Mack Publishing Co., Easton, Pa., 1975. Long-acting, slow-release preparations of the glycopeptide of formula I may also be obtained by microencapsulation in a pharmaceutically acceptable coating material, for example gelatine, polyvinyl alcohol or ethyl cellulose.

Further examples of coating materials and of the processes used for microencapsulation are described by J. A. Herbig in "Encyclopedia of Chemical Technology", Vol. 13, 2nd Ed., Wiley, N.Y., 1967, pp. 436–456. Such formulations, as well as suspensions of salts of the glycopeptide which are only sparingly soluble in body fluids, are designed to release from about 0.1 mcg to about 100 mcg of the glycopeptide per kilogram body weight per day, and are preferably administred by intramuscular injection. Alternatively, some of the solid dosage forms listed above, for example certain sparingly water-soluble salts or dispersions in or adsorbates on solid carriers of the glycopeptide, for example dispersions in a neutral hydrogel of a polymer of ethylene glycol methacrylate or similar monomers cross-linked as described in U.S. Pat. No. 3,551,556 issued Dec. 29, 1970 to K. Kliment et al., may also be formulated in the form of pellets releasing about the same amounts as shown above and may be implanted subcutaneously or intramuscularly.

The following non-limitative Examples will serve to illustrate this invention.

All Beckman ® products, including sperm whale apomyoglobin and sequenator reagents and solvents, as well as the adsorbent 5-Micron Ultrasphere ODS ®, were obtained from Beckman Instruments, Palo Alto, Calif.; all Waters ® products including the Micro-Bondapak C-18 adsorbent were obtained from Waters Associates, Milford, Mass.; Polybrene ® was obtained from Aldrich Chemical Co., Milwaukee, Wis.; all phenylthiohydantion standards were obtained from Pierce Chemical Co., Rockford, Ill.; $^{14}C$-iodoacetamide and the scintillation cocktail Aquasol ® were obtained from New England Nuclear Canada Ltd., Lachine, Quebec; Sequemat ® products were obtained from Sequemat Inc., Watertown, Mass.; ultrafiltration membranes Diaflow UNO5 ® were purchased from Amicon Corporation, Lexington, Mass.; all other chemicals were reagent grade.

EXAMPLE 1

Extraction from Human Pituitaries and Purification of the N-Terminal Fragment of Human Pro-Opiomelanocortin Fresh frozen human pituitaries obtained at autopsy less than 24 hours after death (250 glands, approx. 150 g) were powdered at temperatures below −20° C. and triturated with 600 ml ice-cold water containing 15 ml conc. HCl. To the mixture thus obtained there were added 2500 ml of acetone containing 45 ml conc. HCl previously cooled to −20° C., the resulting suspension was agitated at 4° C. for 1.5 hours and centrifuged at 6000 rpm for 30 minutes. The solids were discarded and the supernatant (2900 ml) was added slowly with stirring to 15 liters acetone previously cooled to −20° C., keeping the mixture at −20° C. during addition and allowing it to settle at −20° C. overnight. The supernatant was removed by decantantion and/or aspiration and discarded, the solids were collected and acetone was evaporated therefrom by a stream of air. Ice-cold water (880 ml) was added while cooling the mixture in an ice bath, and sodium chloride was added to a final concentration of 6 percent (wt/vol) by adding a sufficient amount of saturated NaCl solution. The mixture was adjusted to pH 3.0 with 5N NaOH, stirred for 1 hour at 4° C., and centrifuged at 6000 rpm for 30 minutes. The solids were separated and kept for other uses, and to the supernatant (950 ml) sodium chloride was added to saturation (360 g). The mixture was stirred at 4° C. for 1 hour, centrifuged at 6000 rpm for 30 minutes, the supernatnat was discarded, and the solids were suspended in 300 ml of ice-cold water. The suspension thus obtained was adjusted to pH 3.0 and subjected to ultrafiltration on a Diaflow UMO5 ® ultrafiltration membrane with a cut-off point at a molecular weight of about 500 (Amicon Corporation, Lexington, Mass.) against distilled water at 4° C., and the portion which did not pass through the above membrane was further purified by chromatography on CMC, see below.

Alternatively, the above suspension adjusted to pH 3.0 was dialyzed against distilled water at 4° C., using a Spectrapor ® cellulose membrane with a cut-off point at a molecular weight of about 2500 (Spectrum Medical Industries, Los Angeles, Calif.), and the non-dialyzeable portion thereof was further purified by chromatography on CMC, see below.

The portion which did not pass through the above Diaflow UMO5 ® membrane, or the non-dialyzeable portion, both obtained as described above, was freeze-dried to give about 2.7 g of solids. Said solids were divided into four equal parts, and each part was dissolved in 10–20 ml of 0.01M ammonium acetate buffer at pH 4.6. The solutions thus obtained were centrifuged, the solids discarded, and each of the supernatants was applied to a column (1.5×100 cm) of carboxymethyl cellulose (CMC) previously equilibrated with the same 0.01M ammonium acetate buffer pH 4.6 as above. The columns were eluted with a concave gradient of ammonium acetate from 0.01M at pH 4.6 to 0.1M at pH 6.7, collecting 8 ml fractions and monitoring at 280 nm. The first 20 fractions were collected under isocratic conditions and showed a peak of absorption at 280 nm. Those fractions were combined and freeze-dried, to give the material which was not retained on CMC.

Said last-named material was further purified by HPLC on a semi-preparative column (0.70×25 cm) of Beckman ® 5-Micron Ultrasphere ODS ® using 0.02M triethylammonium formate (TEAF) pH 3.0 as the aqueous buffer and 2-propanol as the organic eluant. A linear gradient starting from 20% 2-propanol:80% TEAF up to 47% 2-propanol:53% TEAF was used at a flow rate of 2 ml/min and a duration of 90 min. The HPLC apparatus used was a Waters liquid chromatograph Model 204 equipped with a waters Model 450 U.V. detector, monitoring absorption at 280 nm. Each peak was collected, lyophylized, and a weighed portion was subjected to quantitative radio-immunoassay using a porcine N-terminal antibody recognizing the gamma-MSH sequence, see FIG. 1A. Based on a standard displacement curve the amount of human N-terminal fragment in each fraction was calculated as a percentage by weight. The peaks denoted V+VI were then repurified under the same conditions and gave the substantially pure N-terminal fragment of human pro-opiomelanocortin, viz., the glycopeptide of formula I, as a colourless, fluffy solid (15 mg). The glycopeptide of formula I is characterized by having a peak of absorption at 280 nm eluted at 32–34 percent 2-propanol and 68–66 percent 0.02M TEAF when subjected to HPLC on a Waters ® Micro-Bondapak C-18 ® column with a gradient of 20 percent to 60 percent 2-propanol over 80 minutes at a flow rate of 1 ml/min., see FIG. 1B. The glycopeptide is further characterized by its amino acid analysis shown in Table 1, by its chemical structure shown in formula I, and by an apparent molecular weight of 16000–18000 as determined by SDS-polyacrylamide gel electrophoresis.

In another experiment 600 g fresh frozen human pituitaries gave about 60 mg of the glycopeptide.

EXAMPLE 2

Amino Acid Analysis

A sample of the glycopeptide obtained as described in Example 1 was reduced and carboxymethylated in the manner described by Crestfield et al. (1963) cited above, and triplicate samples of the material thus obtained were heated to 105° C. for 24, 48, and 72 hours with 5.7M hydrochloric acid in evacuated tubes. The hydrolyrates thus obtained were analyzed on a modified Beckman ® Model 120C amino acid analyzer equipped with a Beckman ® Model 126 computing integrator and the separation of the amino acids was carried out on a column packed with Beckman ® W-3 resin. Results are shown in Table 1.

EXAMPLE 3

Incorporation of $^{14}$C-Iodoacetamide and Sequence Determination

Figure 2:
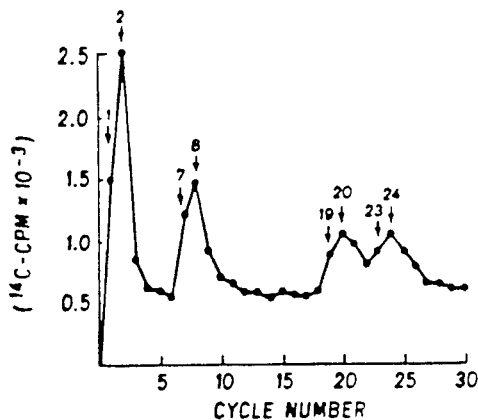
FIG. 2 shows the microsequence of the substantially pure N-terminal fragment of human pro-opiomelanocortin (combined peaks V and VI from FIG. 1A, repurified as in FIG. 1B), labelled with $^{14}$C-iodoacetamide.

A sample of the glycopeptide obtained as described in Example 1 (50 mcg) was treated with dithiothreitol and $^{14}$C-iodoacetamide in the manner described by Crestfield et al. (1963) cited above. The amino acid sequence of the resulting reduced and $^{14}$C-labelled glycopeptide was determined on an updated Beckman ® Model 890B sequenator equipped with a Sequemat ® Model P-6 autoconverter using 0.3M Quadrol ® at pH 9.0 as the sequencer buffer with 2.5 mg sperm whale apomyoglobin and 3 mg Polybrene ® as carriers in the sequenator cup. The individual thiazolinones thus obtained were counted on a Beckman ® liquid scintillation counter using Aquasol ® as the scintillation cocktail. The results are shown in FIG. 2 and the demonstrate the presence of cysteine residues at positions 2, 8, 20, and 24.

EXAMPLE 4

Cyanogen Bromide Cleavage, and Purification of CNBr Fragments

A sample of the native glycopeptide obtained as described in Example 1 (1.4 mg) was dissolved in 0.3 ml of 70% aqueous formic acid and sufficient cyanogen bromide dissolved in acetonitrile was added to give a molar ratio of 1:1000, calculated on the basis of a molecular weight of the glycopeptide of 12000 (see Mains et al. (1979) cited above). The mixture was stirred at room temperature for 24 hours and the reaction was terminated by freeze-drying three times.

The residue thus obtained was subjected to HPLC on a Waters ® Micro-Bondapak C-18 ® column (0.39×30 cm) using 0.02M triethyl ammonium phosphate (TEAP) at pH 3.0 as the aqueous buffer and a linear gradient of 2-propanol, from 5 percent to 60 percent, at a flow rate of 1 ml/min over a period of time of 110 minutes, on a Waters ® Model 204 liquid chromatograph equipped with a model 450 variable U.V./vis. detector and monitoring absorption at 210 nm. Three major peaks of absorption were thus obtained, see FIG. 4. The respective eluates were separately freeze-dried, and each fraction was subjected to the same HPLC procedure as above except that 0.02M triethylammonium formate (TEAF) was used as the aqueous buffer and that absorption was monitored at 220 nm. In this manner there were obtained the three fragments of the glycopeptide designated as CNBr-I, CNBr-II and CNBr-III, respectively, as substantially pure compounds, by repeated freeze-drying of the respective eluates from the HPLC column.

The amino acid analyses of the above three fragments CNBr-I, CNBr-II, and CNBr-III were carried out as described in Example 2 and are shown in Table 3. The amino acid sequences of the fragments CNBr-II and CNBr-III were carried out as described in Example 5 and are shown in FIGS. 5 and 6, respectively.

EXAMPLE 5

Determination of Amino Acid Sequences

The sequence determinations of the reduced and carboxymethylated glycopeptide obtained as described in Examples 1 and 2 and of the fragments CNBr-II and CNBr-III obtained as described in Example 4 were performed on an updated Beckman ® Model 890B sequenator using 0.3M Quadrol ® pH 9 as sequencer buffer and adding 3 mg Polybrene ® together with 100 nMoles of the dipeptide Leu-Val to the cup and performing 7 dummy cycles. The peptide to be sequenced was then added and double coupling was performed for the first cycle only. The program used was Beckman's 0.1M Quadrol with $S_1+S_2$ wash #12.11.78. The sequenator was equipped with a Sequemat ® P-6 autoconverter and thus all conversions were done automaticaly immediately following the cleavage step using 1.5N HC/MeOH at 65° C. The phenylthiohydantoin (PTH) derivatives of the amino acids were separated on a Beckman ® 5-Micron Ultrasphere ODS ® colum (0.46×25 cm) in the manner described by Somack (1980) cited above except that PTH-Glu, PTH-Asp and PTH-S-carboxymethyl cysteine were detected as their respective methyl esters and PTH-NorLeu was used as an internal standard. The Waters model 204 liquid chromatograph used was equipped with a Wisp ® 710 autoinjector, a Data ® Module 730 integrator plotter and a 720 system controller (all Waters products). Results of the sequence determination of the reduced and carboxymethylated glycopeptide are shown in FIG. 3, and those of the fragments CNBr-II and CNBr-III are shown in FIGS. 5 and 6, respectively.

EXAMPLE 6

Determination of C-Terminal Amino Acid Residue by Carboxypeptidase Y Digestion

A sample of the reduced and carboxymethylated glycopeptide obtained as described in Examples 1 and 2 was dissolved in 0.1M pyridine/acetate buffer pH 5.5, 5 mcg of carboxypeptidase Y (Boehringer-Mannheim) was added giving a final ratio of enzyme to peptide of 1:100 (wt:wt). The mixture was incubated at 37° C., and at intervals of 15, 30, 60, and 120 minutes aliquots were removed, boiled for 5 minutes at 100° C. to inactivate the enzyme and then immediately lyophilized. Amino acid analysis of these four aliquots was then performed. Only insignificant amounts of amino acids, too small to be identifiable, were released at 15 minutes. However, glutamine was the first amino acid released and identified after 30 minutes incubation, thus showing that glutamine was the carboxy-terminal residue.

EXAMPLE 7

Digestion of Fragment CNBr-I with Staphylococcal Protease V8

A sample of the purified fragment CNBr-I obtained as described in Example 4 (200 mcg) was dissolved in 0.05M $NH_4HCO_3$ at pH 7.9 and incubated at 37° C. for 24 hours with 10 mcg of staphyloccal protease V8 (obtained from Dr. G. Drapeau, Université de Montréal, Montreal, Canada). Following lyophylization, the products of digestion were purified by HPLC on a Waters Micro-Bondapak C-18 ® column (0.39 and 30 cm) using a 0.02M triethylamine phosphate pH 3.0/acetonitrile linear gradient of 2% $CH_3CN$ to 56% $CH_3CN$ for 120 minutes at 1 ml/min. The purified peptides were collected, lyophilized, hydrolysed for 24 hrs and their amino acid analyses determined. Results are shown in Table 3.

EXAMPLE 8

Stimulation of Aldosterone Production

A primary aldosteronoma of 2.6 cm size adjacent to a normal adrenal cortex was surgically removed from a female hypertensive patient showing elevated (50–72 ng%) plasma aldosterone levels. The tumor tissue was cut into small pieces (1 $mm^3$) and the cells were enzymatically dispersed and filtered in the manner described by Lis et al. (1981) J. Clin. End. Metab. 52, 1053–1056. The cell suspension was distributed in 0.2 ml aliquots into Linbro 96-well microtitration plates (Linbro Chemical Co., New Haven, CT) coated with collagen and the cells left in the incubator overnight to attach. These cells were then kept in culture in a medium containing 10% fetal bovine serum for 24 days. For the preincubation and the incubation period the same medium was used except that fetal bovine serum was replaced by bovine serum albumin in a concentration of 0.5 mg/ml. Attached cells were washed, preincubated for 1 hour and then incubated for 2 hours in the presence of different concentrations of the human glycopeptide obtained as described in Example 1, the homologous porcine N-terminal peptide described by Larivière et al. (1980) cited above and synthetic ACTH 1-24 (Organon canada Ltd., West Hill, Ontario, Canada). Aliquots of 0.1 ml of medium were collected for aldosterone measurements by the specific radioimmunoassay described by Vecsei cited above. The aldosterone antibody was a gift from Dr. P. Vecsei, Heidelberg, West Germany, and tritiated aldosterone tracer was purchased frm NEN Canada Ltd., Lachine, Quebec. Results are shown in Table 4.

The embodiments of the invention in which an exclusive property or privilege is claimed are defined as follows:

1. The N-terminal fragment of human proopiomelanocortin, viz., the glycopeptide of the formula I

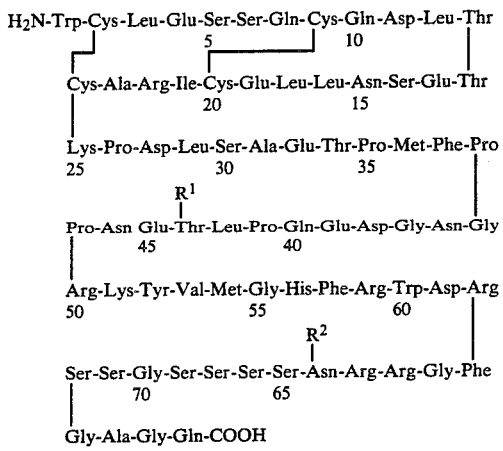

in which the disulfide bridges are indicated by the symbol ⌐⌐⌐⌐, $R^1$ represents a glycosyl residue attached to threonine in position 45 of an O-glycosidic linkage and containing glucosamine and galactosamine in a ratio of about 1:2, and $R^2$ represents a glycosyl residue attached to asparagine in position 65 by an N-glycosidic linkage and containing glucosamine and galactosamine in a ratio of about 3:1;

having the following amino acid composition and integer values: Asp+Asn=Asx (8), Thr (4), Ser (10), Glu+Gln=Glx (10) Pro (5), Gly (7), Ala (3), Cys (4), Val (1), Met (2), Ile (1), Leu (6), Tyr (1), Phe (3), His (1), Lys (2), Trp (2), Arg (6);; and having a peak of absorption at 280 nm eluted at 32–34 percent 2-propanol and 68–66 percent 0.02M triethylammonium formate when subjected to HPLC on a micro-Bondapak C-18 ® column wit a gradient of 20 percent to 60 percent 2-propanol over 80 minutes at a flow rate of 1 milliliter per minute, as well as an apparent molecular weight of 16000–18000 as determined by SDS-polyacrylamide gel electrophoresis.

2. An N-terminal fragment of human pro-opiomelanocortin according to claim 1 prepared by a process comprising in sequence the following steps:

(a) triturating human pituitaries with about 20 parts wt/vol of acqueous acetone containing 20 ml concentrated hydrochloric acid per liter, and separating the solids to obtain a supernatant; adding said supernatant to 5 volumes of acetone to obtain a solid;

(b) dissolving said last-named solid in water, adding sufficient sodium chloride to obtain a concentration of 6 percent NaCl, and separating the solids to obtain a supernatant, adding sodium chloride to said last-named supernatant, and separating the solids thus obtained;

(c) suspending said last-named solids in water and either (1) subjecting the suspension thus obtained to ultrafiltration against distilled water and collecting the portion of said suspension which is retained on the ultrafilter; or (2) dialyzing the above suspension against distilled water and collecting the non-dialyzeable portion thereof; and freeze-drying said portion which is retained on the ultrafilter, or said non-dialyzable portion, to obtain a freeze-dried solid;

(d) applying said last-named freeze-dried solid in solution in ammonium acetate buffer to a column of carboxymethyl cellulose, eluting said column with ammonium acetate buffer, and collecting the material which is not retained on carboxymethyl cellulose;

(e) purifying said last-named material which is not retained on carbomethyl cellulose by high performance liquid chromatography on a column of an alkylsilane supported on glass beads, using an aqueous volatile alkylamine buffer and a linear gradient of a water-miscible lower alkanol as the organic eluant, collecting the eluates containing the N-terminal fragment of human pro-opiomelanocortin and freeze-drying same, to obtain the N-terminal fragment of human pro-opiomelanocortin.

* * * * *